United States Patent [19]

Ballas et al.

[11] Patent Number: 4,812,395

[45] Date of Patent: Mar. 14, 1989

[54] METHOD FOR DETECTING ENZYMATIC ACTIVITY USING PARTICLE AGGLUTINATION

[75] Inventors: Robert A. Ballas, Newark; William A. Frey, Wilmington, both of Del.

[73] Assignee: E. I. Du Pont De Nemours and Company, Wilmington, Del.

[21] Appl. No.: 877,998

[22] Filed: Aug. 19, 1986

Related U.S. Application Data

[62] Division of Ser. No. 668,489, Nov. 5, 1984, abandoned.

[51] Int. Cl.$^4$ ............... G01N 33/546; G01N 33/547; G01N 53/00
[52] U.S. Cl. .......................... 435/7; 435/12; 435/18; 435/21; 435/25; 435/28; 436/501; 436/518; 436/529; 436/533; 436/534; 436/805
[58] Field of Search ............... 435/4, 7 R, 18, 21, 435/25, 28, 23, 24; 436/501, 518, 529, 533, 534, 805

[56] References Cited

U.S. PATENT DOCUMENTS

| | | | |
|---|---|---|---|
| Re. 29,169 | 4/1977 | Schuurs et al. | 435/7 |
| 3,791,932 | 2/1974 | Schuurs, et al. | 435/7 |
| 4,288,538 | 9/1981 | Groman et al. | 435/7 |
| 4,355,102 | 10/1982 | Quash | 435/7 |
| 4,401,765 | 8/1983 | Craig et al. | 436/533 |
| 4,551,426 | 11/1985 | Freytag et al. | 435/14 |
| 4,663,278 | 5/1987 | Dinello | 435/7 |

FOREIGN PATENT DOCUMENTS 0018731 11/1980 European Pat. Off. .

OTHER PUBLICATIONS

Ballas et al, *Chem Abs*, 105, 936113, 1986.
Yellow, R. S. and Berson, A. A., 1959, *Nature*, 184:1648–1649.
Van Weeman, B. K. et al., 1971, *FEBS Letters*, 15(3):232–236.

*Primary Examiner*—Robert J. Warden
*Assistant Examiner*—David A. Saunders
*Attorney, Agent, or Firm*—George A. Frank

[57] ABSTRACT

A method is disclosed for determining enzymatic activity in a liquid sample by particle agglutination or inhibition of particle agglutination.

21 Claims, No Drawings

METHOD FOR DETECTING ENZYMATIC ACTIVITY USING PARTICLE AGGLUTINATION

This is a division of application Ser. No. 668,489, filed Nov. 5, 1984, now abandoned.

TECHNICAL FIELD

This invention relates to particle agglutination based diagnostic methods for detecting enzymatic activity in liquid test samples.

BACKGROUND ART

It is known that the reaction of an enzyme with its substrate generates a product. The enzyme is a true catalyst because it is not consumed in the reaction, but is free to generate repetitively more product. The rate at which the product is generated is referred to as the turnover number, a number that varies for different enzymes. In practice, enzymatic activity is most conveniently detected by monitoring a spectrophotometric absorbance of the substrate or product that varies as a result of enzymatic turnover. It is known that some naturally occurring substrates and/or their corresponding products do not possess readily utilizable absorbance peaks, making the spectrophotometric detection of enzymatic activity difficult. In some cases a synthetic substrate can be designed for the detection of enzymatic activity.

Synthetic substrates can be designed to be chromogenic or fluorogenic, i.e., when catalyzed by the enzyme, an optionally detectable change in the substrate and/or product is produced. The most significant limitation to the use of synthetic substrates to detect enzymatic activity is that such substrates cannot always be prepared for the desired enzyme. Detailed knowledge is required of the catalytic properties of each specific enzyme in order to properly design a useful synthetic substrate. For example, synthetic chromogenic substrates for thrombin or Factor $X_a$ have been designed for the detection of thrombin or Factor $X_a$ activity. These synthetic substrates replace the natural substrate, fibrinogen, in chromogenically based assays for these enzymes.

Immunoassays for the detection of analytes are known. The so-called heterogeneous immunoassays can involve an incubation of an antibody with the analyte in the presence of a labeled antigen of substantially identical immunological properties vis a' vis the antibody as the analyte. The amount of labeled antigen bound to the antibody or free in solution is determined after an appropriate separation procedure, as a measure of the amount of analyte present. The first such assay was described by R. S. Yalow and S. A. Berson in 1959 (Nature 184:1648). This assay, called a radioimmunoassay, utilized a radionuclide as the label. The use of enzymes as labels to replace the radionuclide with the latter's self-evident storage, handling and safety problems, was described by van Weemen and Schuurs in 1971 (FEBS Letters, Volume 15, 232 (1971) and U.S. Pat. No. 3,791,932, issued Feb. 12, 1974 on an application filed Jan. 27, 1972). The art has seen numerous variations on the basic theme of van Weemen and Schuurs.

It is known that multiepitopic antigenic substances can agglutinate particles with multiple epitope receptors to produce agglomerates, e.g., influenza virus and sheep erythrocytes, respectively. These agglomerates can be detected using light scattering type measurements. Agglutination-inhibition assays are known for the detection of antigens and haptens in liquid test samples. Typically, the binding of a multivalent antibody to highly refractive particles coated with the antigen or hapten is inhibited in a competitive fashion by the antigen or hapten in the test sample. (See Craig et al., U.S. Pat. No. 4,401,765 issued Aug. 30, 1983.) These assays are generally limited in sensitivity to antigens and haptens in the concentration range of $10^{-7}$ to $10^{-9}$ M.

A continuing problem in immunoassays utilizing enzymes as labels is the inability to detect analytes at concentrations below $10^{-10}$M in a relatively short period of time, typically thirty minutes or less, preferably ten minutes or less. High turnover number enzymes have been used as labels to maximize signal production. Such enzymes include $\beta$-galactosidase, horseradish peroxidase, alkaline phosphatase, glucose oxidase, $\beta$-lactamase, and urease. The use of chromogenic substrates with these enzymes can provide sensitivity to about $10^{-10}$M. The use of fluorogenic substrates could lead to even greater sensitivity. However, all biological samples contain fluorescent material, e.g., porphyrins, which can interfere with the fluorogenic substrate measurements. This disadvantage can be overcome with additional sample processing, specifically, separating the bound from enzyme-labeled complex. Interfering fluorescent materials can be removed during this separation, with the constraint that measurements of only the bound enzyme-labeled complex can be made.

High sensitivity immunoassays using enzyme require an undesirable amount of time for the generation of detectable levels of enzymatically generated chromophore or fluorophore, i.e., roughly thirty to ninety minutes to achieve optimum sensitivity, even with high turnover number enzymes and synthetic substrates.

There is a continuing need in the art for a method to detect low levels of enzymatic activity in a test sample in a short amount of time, typically ten minutes or less. There is also a need for a method to measure enzymatic activity when no readily measurable product results from either natural or synthetic substrates.

DISCLOSURE OF THE INVENTION

This need is met by the present invention which, in a first aspect is an agglutination based method for detecting an enzyme in a liquid test sample, comprising:

(1) forming an agglutination system comprising:
 (i) highly refractive particles having a ligand disposed thereon,
 (ii) a binding partner specific for the ligand and capable of binding to at least two ligands, the binding partner and ligand being present at concentrations which permit agglutination, and
 (iii) a substrate for the enzyme, the enzyme, substrate, ligand and binding partner being such that a reaction between the enzyme and substrate produces a product which competes with the ligand for the binding partner;

(2) contacting the agglutination system with the test sample to produce the product which competes with the ligand for the binding partner;

(3) measuring a physical property of the agglutination system, which property is a function of agglutination; and (4) relating the measurement to the amount of enzyme initially present in the test sample.

In a second aspect the present invention is an agglutination based assay for detecting an analyte in a liquid test sample, comprising:

(1) contacting the sample with a conjugate comprising an enzyme and a first binding partner capable of binding to the analyte, whereby a fraction of the conjugate binds to the analyte to form a complex and a fraction of the conjugate remains free;

(2) separating the free conjugate from the complex;

(3) contacting either the free conjugate or the complex with an agglutination system comprising:
  (i) highly refractive particles having a ligand disposed thereon,
  (ii) a second binding partner capable of binding to at least two ligands, the second binding partner and ligand being present at concentrations which permit agglutination, and
  (iii) a substrate for the enzyme, the enzyme, substrate, ligand and second binding partner being such that a reaction between the enzyme and substrate produces a product which competes with the ligand for the second binding power;

(4) measuring a physical property of the agglutination system, which property is a function of agglutination; and (5) relating the measurement to the amount of analyte initially present in the liquid test sample.

In a third aspect, the present invention is an agglutination based method for detecting an enzyme in a liquid test sample, comprising:

(1) forming an agglutination system comprising:
  (i) highly refractive particles having coated thereon a substrate capable of being converted into a ligand upon reaction with the enzyme; and
  (ii) a binding partner capable of binding to at least two ligands, but incapable of binding to the substrate;

(2) contacting the agglutination system with the sample to convert the substrate into the ligand;

(3) measuring a physical property of the agglutination system which is a function of agglutination; and (4) relating the measurement to the amount of enzyme initially present in the test sample.

In a fourth aspect, the present invention is an agglutination based method for detecting an analyte in a liquid test sample, comprising:

(1) contacting the sample with a conjugate comprising an enzyme and a first binding partner capable of binding to the analyte, whereby a fraction of the conjugate binds to the analyte to form a complex and a fraction of the conjugate remains free;

(2) separating the free conjugate from the complex;

(3) contacting either the free conjugate or the complex with an agglutination system comprising:
  (i) highly refractive particles having coated thereon a substrate capable of being converted into a ligand upon reaction with the enzyme; and
  (ii) a binding partner capable of binding to at least two ligands, but incapable of binding to the substrate;

(4) measuring a physical property of the agglutination system which is a function of agglutination; and (5) relating the measurement to the amount of enzyme initially present in the test sample.

DETAILED DESCRIPTION OF THE INVENTION

In an inhibition mode, the present invention makes use of an agglutination system which comprises highly refractive particles having a bindable substance, i.e., a ligand, on their surfaces. A binding partner specifically reactive with the ligand is reacted with the particles. The binding partner is multivalent, i.e, can bind with at least two ligands. The binding partner is used at a concentration which provides substantial agglutination of the highly refractive particles. Agglutination occurs because the multivalent binding partner can act as a crosslinking agent to link two particles together. The agglutination system also contains a substrate for the enzyme to be detected. The substrate, enzyme and ligand must be chosen to form an operational trio. Specifically, given the enzyme to be detected, the ligand must be chosen to have substantially identical properties vis a' vis the binding partner as the product of the enzyme-substrate reaction. This condition assures that the product of the enzyme-substrate reaction will compare with the ligand for the binding partner, thus reducing the amount of binding partner available to participate in the agglutination reaction. In operation, the test sample is contacted with the agglutination system and the amount of subsequent agglutination inhibition determined in comparison with an enzyme-free control. In one aspect, the enzyme can be free in solution and the amount of enzyme can be determined by either direct agglutination or agglutination inhibition. Alternatively, the enzyme can be a label on an antibody molecule, antigen or hapten molecule, nucleic acid probe, etc., in which case the inhibition of agglutination is a direct measure of the substance on which it acts as a label. In one example of the latter case, the sample containing the analyte is contacted with a conjugate of the enzyme and a binding partner reactive with the analyte. The conjugate can be prepared prior to contact with the sample by covalent bonding between the enzyme and the substance on which it acts as a label. This conjugate is prepared by known methods that provide attachment of enzyme to the binding partner either directly or through an appropriate spacer arm, and which preserve both enzyme activity and the ability of the binding partner to bind its corresponding analyte. It is also possible to prepare appropriate conjugate by other means including the specific bonding of avidin-labelled enzyme and biotin-labelled binding partner in instances when direct covalent attachment of enzyme to antibody is undesirable. This avidin/biotin labeling allows for preparation of conjugate formed by incubation of labeled enzyme and analyte binding partner prior to contact with the sample or during simultaneous contact with the sample. Alternatively, the conjugate of enzyme and binding partner can be formed in a sequential manner by adding sample, labeled binding partner, and labeled enzyme in any desired order. In all cases, the total number of binding sites provided by the binding partner is in molar excess relative to the analyte. A fraction of the conjugate binds to the analyte, and the remaining fraction remains free. Either the bound or the free conjugate is contacted with the agglutination system to inhibit agglutination.

In a direct agglutination mode, the highly refractive particles have disposed on their surfaces the substrate for the enzyme, rather than the ligand. When the particles are reacted with the enzyme, the substrate is converted into the ligand. The binding partner is then able to cross-link separate particles to provide agglutination. Again, the enzyme can exist free in the test sample, in which case the agglutination phenomenon is a direct measure of the enzyme, or the enzyme can be the label on an antibody, antigen or hapten, nucleic acid probe, etc., in which case the agglutination phenomenon is an indirect measure of the substance on which it acts as a label.

Enzymes which can be detected using the method of the present invention include, but are not limited to, $\beta$-galactosidase, alkaline phosphatase, horseradish peroxidase, glucose oxidase, urease and $\beta$-lactamase. When used as an indirect measure of a substance in a biological sample, such test samples can include blood, cerebrospinal fluid, serum, plasma, sputum, urine, nasal washings, genital and throat swabs, and other biological samples.

Suitable highly refractive particles can be made from, for example, agarose, polydextran, polyacrylamide and polymeric latexes. Particle shape is not critical, although spherical particles are preferred because they are easiest to prepare and provide maximum lattice density in the agglutinated state. Particle size is somewhat critical. Preferred diameter for spherical particles is from about 30 nm to 100 nm for the agglutination inhibition mode. The most preferred particle is that described in U.S. Pat. No. 4,401,765, issued to Craig et al. on Aug. 30, 1983 on an application filed Oct. 28, 1981. The disclosure of this patent is incorporated herein by reference. These particles have a highly refractive spherical polymer core preferably made of polyvinylnaphthalene and polystyrene. The core has disposed on its surface a reactive shell to which antigens, haptens, etc., can be covalently coupled. A convenient way to control particle size of the polymer particles is first to prepare a seed emulsion whose size can be controlled by the amount of surfactant used. After preparation of the seed emulsion, additional monomer and surfactant can be added at a controlled rate to increase the size of the particles in the seed emulsion.

The outer shell polymer of the polymer particle can be prepared from a wide range of ethylenically unsaturated monomers having functional groups capable of reacting with compounds of biological interest. Optionally, the outer shell can also contain other ethylenically unsaturated monomers. The attachment of the shell polymer to the core can be accomplished by graft polymerization of the functional monomer to the residual ethylenically unsaturated groups in the core polymer or the functional monomer can be polymerized around the core to produce a contiguous shell. Preferred monomers include those containing an epoxy group such as glycidylmethacrylate, glycidyl acrylate, vinyl glycidyl ether, and methallyl glycidyl ether. Other functional groups include carboxyl, hydroxyl, amino, and aldehyde.

Particles having diameters greater than 100 nm, preferably in the range of 1000 nm to 100,000 nm can be prepared for visual agglutination tests according to methods previously described. These larger diameter particles are readily seen during agglutination reactions due to changes in their agglutination state. The direct agglutination mode is preferred for visual detection of particle aggregation because direct agglutination is easier to detect than agglutination inhibition.

In the inhibition mode, the particles having the desired composition are prepared with appropriate ligands disposed on their surfaces. The ligand can be physically adsorbed or covalently attached (directly or through a so-called spacer arm). Methods for covalently attaching compounds to derivatized surfaces are well known. [Kiefer, Immunological Methods, Lefkovits & Perris, eds., New York: Academic Press, 1979, 137] In the direct agglutination mode, the particles have the substrate disposed on their surfaces. Methods of covalently attaching substrate are analogous to those for attaching ligand.

To practice the agglutination inhibition mode of the present invention, the enzyme substrate reaction must produce a product which competes with the ligand for the binding partner. Additionally, the substrate must not be substantially reactive with the binding partner prior to enzymatic cleavage. For exmaple, in the case of $\beta$-galactosidase, a suitable substrate is ortho-nitrophenyl-$\beta$-galactopyranoside (ONPG), and a suitable binding agent is an anti-ortho-nitrophenol or an anti-nitrohydroxybenzoic acid (NHB) antibody. When $\beta$-galactosidase reacts with ortho-nitrophenyl-$\beta$-galactopyranoside, the bond between the ortho-nitrophenyl group and the $\beta$-galactopyranoside moiety is cleaved, yielding a free ortho-nitrophenol molecule. The antibody is reactive with the ortho-nitrophenol molecule, but not with ortho-nitrophenyl-$\beta$-galactopyranoside. It is believed that the galactopyranoside group sterically prevents the binding of the anti-ortho-nitrophenol antibody with the ortho-nitrophenyl substituent (ONP). However, enzymatic cleavage of substrate produces a product which is capable of binding with the antibody. The required functional relationship between enzyme, substrate, ligand, and binding partner is further illustrated by the data in Table 1 which shows a comparison of agglutination rates provided by substrate and product.

The data were gathered by comparing the ability of ONPG and 3-nitro-4-hydroxybenzoic acid (NHB), an ONP analogue, to inhibit the agglutination of NHB-coated particles by an anti-NHB antibody. The data show that concentrations of NHB approximately three orders of magnitude below those of ortho-nitrophenyl-galactopyranoside produce equivalent inhibition. NHB is the functional equivalent to the product resulting from hydrolysis of ONPG by $\beta$-galactosidase. Therefore, there is no significant inhibition of agglutination absent the enzymatic cleavage of substrate.

TABLE 1

| Agglutination Inhibition of NHB-bearing Particles by Enzyme Substrate (ONPG) and Product (NHB) | | |
|---|---|---|
| ONPG or NHB Concentration (Mole/liter) | Agglutination Rate (mA/minute; 405 nm) | |
| | NHB | ONPG |
| 0 | 353 | 387 |
| $10^{-9}$ | 331 | 405 |
| $10^{-8}$ | 243 | 411 |
| $10^{-7}$ | 102 | 408 |
| $10^{-6}$ | 18 | 384 |
| $10^{-5}$ | 0 | 360 |
| $10^{-4}$ | 0 | 178 |
| $10^{-3}$ | 0 | 24 |

It will be appreciated by those skilled in the art that to demonstrate a maximally sensitive quantitative assay system with any operational trio of substrate, enzyme, and ligand, certain requirements must be met. The substrate must be in molar excess relative to the anticipated concentration of enzyme. Typically, substrate concentration is on the order of 5 to 10 $K_m$ (Michaelis constant). This requirement generally insures that first-order kinetics are observed with respect to substrate, and that reaction rate is not limited by insufficient substrate concentration. When the enzyme of interest occurs in the assay as a reagent, the determination of appropriate substrate level is relatively straight-forward because the enzyme will occur in the system over an expected concentration range. When the enzyme of interest is the assay analyte and is also rare or difficult to isolate, a more empirical approximation of appropriate substrate level may be required to maintain favorable kinetics for a quantitative assay. The constraints in the relationship of enzyme and substrate levels just discussed are not as critical for qualitative results where the presence or absence of enzyme may be of interest.

Another important consideration is the degree of cross-reactivity of binding partner with substrate. The selected level of substrate that insures first-order kinetics in quantitative and semi-quantitative systems, also insures that substrate will occur in much greater concentration than product being produced by enzyme activity. The law of mass action would suggest binding of binding partner to substrate if significant cross-reactivity existed. This would result in significant background agglutination in direct agglutination systems, and unacceptable levels of non-specific inhibition of agglutination in inhibition systems. Therefore, to achieve maximal assay sensitivity, binding partner is selected with little or no cross-reactivity with substrate when at least a 2 to 3 order of magnitude concentration difference exists between substrate and product. This requirement provides that in direct agglutination systems, very low levels of product can be detected, and in inhibition systems, very low levels of product compete effectively with particle-bound ligand for binding partner combining sites. In both systems, a noticeable change in particle agglutination state can be observed with very low levels of product only when binding partner cross-reactivity is minimized. Under quantitative conditions for most enzymes, substrate concentrations will range from $10^{-13}$ to $10^{-6}$M, and product will range from approximately $10^{-6}$ to $10^{-10}$M.

In the direct agglutination mode which requires the substrate to be disposed on the surface of the highly refractive particle, it is important that the cleavable bond not be sterically hindered from the enzyme by the particle itself. The use of a so-called spacer arm can provide sufficient distance between the cleavable bond and the particle surface to prevent hindrance.

Preferred binding agents are antibody molecules. Antibodies are known to be highly specific for their respective antigens or haptens. In addition, antibodies are easily prepared and provide the multivalency required for agglutination. Both monoclonal and polyclonal antibodies can be used in the present invention.

Antisera or other body fluids such as ascites containing the anti-ligand antibody can be used directly in the agglutination system or can be purified to provide an immunoglobulin fraction, an IgG fraction, or an affinity purified IgG fraction, all of which can also be used as the binding partner in the agglutination system. It is also possible to use an IgM fraction. Fragments of IgG can also be used, e.g., F(ab')$_2$.

Given the choice of a particular enzyme to be detected, the type of cleavable bond can be ascertained, e.g., for $\beta$-galactosidase, the bond is a $\beta(1-4)$ ether linkage between $\beta$-galactopyranoside and another sugar (glucose or fructose) or a suitable substitute such as ONP. A natural substrate containing the bond can be identified or a synthetic substrate containing the bond can be devised. One can then determine the chemical identity of the product(s) resulting from the reaction of the enzyme and substrate, which in turn provides the identity of suitable binding partner and ligand that must be chosen to form an operative system. Specifically, the reaction of enzyme with substrate must produce a product which can compete with the ligand for the binding partner. Examples of operative systems of enzyme, substrate, ligand and binding partner are shown in the table below:

TABLE 2

| Enzyme | Substrate | Ligand | Binding Agent |
| --- | --- | --- | --- |
| $\beta$-galactosidase | ONP—$\beta$-galactopyranoside | Ortho-nitrophenol | Anti-ortho-nitrophenol |
| Alkaline phosphatase | p-nitrophenyl-phosphate | para-nitrophenol | Anti-para-nitrophenol |
| Tyrosine-amino-transferase | tyrosine | p-hydroxyphenyl-pyruvic acid | Anti-p-hydroxy-phenylpyruvic acid |
| | $\gamma$-oxoglutarate | glutamic acid | Anti-glutamic acid |
| Tyrosine decarboxylase | tyrosine | tyramine | Anti-tyramine |
| Biotinyl-CoA—Synthetase | biotin-CoA—ATP | biotin-C—S—CoA | Anti-thioacetyl-CoA |
| $\beta$-galactosidase | galacto-pyranosyl derivatives of aromatic hydroxyl group of thyroxine | thyroxine | Thyroxine Binding Globulin |
| Acetylcholine-sterase | biotinylcholine | biotin | avidin |

Preferred systems are:

(1) $\beta$-galactosidase, ONP-$\beta$-galactopyranoside, ortho-nitrophenol and anti-ortho-nitrophenol antibody; and (2) alkaline phosphatase, p-nitrophenyl-phosphate, paranitrophenol and anti-para-nitrophenol antibody.

As can be seen from the table above, the substrate must provide at least one bond which can be cleaved by the enzyme to yield at least one product which is reactive with the binding partner. One of the products will be chosen to serve as the ligand. In general, the ligand will be a hapten, i.e., a small molecule which can be bound by an anti-hapten antibody, but which cannot directly elicit an immune response. The ligand can be coupled by known methods to a suitable high molecular weight carrier to form an appropriate immunogen. The immunogen can be injected into an immunocompetent animal to elicit an anti-hapten immune response. The immunized animal may then provide suitable antiserum after an appropriate immunization schedule, or suitable immunosensitized cells for use in a recognized monoclonal antibody producing process such as that of Kohler and Milstein [Nature, 256:495, 1975].

Multivalent binding agents other than antibodies can be useable in the present invention, provided that for a given enzyme to be detected, a substrate can be designed to provide a cleavage product which can function as a ligand for the binding agent. For example, thyroxine binding globulin (TBG) is known to bind thyroxine. If one desires to detect a β-galactosidase a substrate comprising a covalent conjugate of thyroxine and galactopyranoside may be designed so that the reaction of the enzyme and substrate yields thyroxine which can be bound by TBG. It is believed that an ether linkage formed from the hydroxyl group of thyroxine and the hydroxyl group of the $C_1$ carbon of galactopyranoside will provide a suitable substrate. Other multivalent binding agents which may prove to be useful in the invention include C-reactive protein, avidin, and amyloid A protein.

In either the direct agglutination or agglutination inhibition modes, the physical properties of the system, especially optical properties, will change with time. Examples of these detectable physical properties include absorbance at a given wavelength of incident light and the intensity of monochromatic light scattered at a selected angle relative to the incident beam. In addition, the size distribution of aggregated, highly refractive particles can be determined.

Absorbance at a given wavelength can be measured using a standard spectrophotometer. Light scattering can be measured using a nephelometer. Size distribution of aggregated, high refractive index particles can be measured using an optically-based or electrically-based particle counter. The preferred method is the measurement of absorbance at a selected wavelength chosen on the basis of high turbidimetric signal and low interference by additional components of the test system. For example, when the system of this invention comprises β-galactosidase, ONP-β-galactopyranoside, ortho-nitrophenol, and anti-nitrophenol antibody, the substrate has a significant absorbance maximum at 340 nm. Therefore, a source of interference would be created by the substrate if the reaction system were monitored at 340 nm, which is the optimal wavelength for measuring the turbidimetric signal. As a result, the turbidimetric signal is monitored at 405 nm to diminish the absorbance contribution from the substrate.

The invention is illustrated by the following nonlimiting examples.

EXAMPLE 1

Measurement of β-galactosidase Activity

The following example illustrates the ability of the method provided by the present invention to measure as little as $2.5 \times 10^{-4}$ units per mL of β-galactosidase within four minutes. In the example, the highly refractive particle used was a polystyrene core with an intermediate shell of polyvinylnaphthalene and an outer shell of polyglycidylmethacrylate. The binding agent was an antibody prepared against the hapten 3-nitro-4-hydroxybenzoic acid. The antibody cross-reacted significantly with ortho-nitrophenol. The ligand was 3-nitro-4-hydroxy- benzoic acid, which was coupled covalently through the carboxyl group to the outer shell of polyglycidyl methacrylate on the highly refractive particles. The substrate for β-galactosidase was ortho-nitrophenyl-β-D-galactopyranoside. The method was performed in the agglutination inhibition mode. The rate of agglutination was determined by measuring the absorbance at 405 nm at two predetermined times.

A. Synthesis of NHB:Protein Conjugates

Keyhole limpet hemocyanin (KLH) (750 mg, Calbiochem-Behring) was dissolved in 10 mL of 0.05M sodium bicarbonate buffer (pH 9.0) and dialyzed exhaustively with the bicarbonate buffer. An analog of ONP, 3-nitro-4-hydroxybenzoic acid (NHB), (64 mg), was dissolved in 5 mL of dimethyl formamide and cooled to 4° C. To this solution was added 81 mg of 1-ethyl-3-(3-dimethylaminopropyl) carbodiimide and 43 mg of N-hydroxysuccinimide. The solution was stirred at 4° C. for 18 hours. The dialyzed KLH solution was then added to the dimethyl formamide solution, the pH was adjusted to 8.5 with 0.2N sodium hydroxide, and the solution was incubated at 4° C. for 8 hours. The reaction mixture was then dialyzed with deionized water to remove unreacted materials and the conjugate was lyophilized prior to storage at 4° C.

A separate conjugate using bovine serum albumin (BSA) as the carrier protein was prepared in an identical procedure using 500 mg of BSA.

B. Polyclonal Anti-NHB Antibodies

Three rabbits (New Zealand White, female) were injected subcutaneously with 0.25 mg of the NHB:KLH conjugate (synthesized in part A above) emulsified in 1.0 mL of complete Freund's adjuvant. Three booster injections were given at approximately 21-day intervals as described above using incomplete Freund's adjuvant. Prior to each booster injection, the rabbits were bled and the serum tested for o-nitrophenol cross-reactive antibodies by a particleenhanced turbidimetric inhibition immunoassay as described in U.S. Pat. No. 4,401,765, using the polymer particle reagent described in part D below.

C. Preparation of Polyvinylnaphthalene/Polyglycidyl Methacrylate Core/Shell Polymer Particles A polystyrene emulsion was prepared at room temperature (20° C.) in a 4L Erlenmeyer flask. The following ingredients were added sequentially: 400 g of Dupanol WAQE [a Du Pont grade of a 30% sodium dodecyl sulfate (SDS) solution] was added to 2.5 L of deionized water, followed by 50 mL of styrene, 20 g sodium metabisulfite, 10 g of potassium persulfate (dissolved in 200 mL of water) and 125 mL of a ferrous sulfate solution (0.6 g of ferrous sulfate heptahydrate, and 0.25 g of sulfuric acid dissolved in 500 mL of nitrogen purged deionized water). The emulsion mixture was stirred and blanketed with nitrogen. After 10 minutes, 25 g of Aerosol OT-100 (American Cyanamid Co., Wayne, N.J.) dissolved in 375 mL of styrene was added at a rate of 30 mL/min. The mixture was stirred overnight. A sample of the emulsion, diluted 1:100, had an optical density of 0.171 at 340 nm.

Polyvinylnaphthalene was prepared in a 250 mL round-bottom flask equipped with a magnetic stirrer and a reflux condenser. The round-bottom flask was placed in a boiling water bath. To provide a polyvinylnaphthalene intermediate shell on polystyrene core particles, 1.8 mL of the polystyrene emulsion, prepared above, was added to 98 mL of water, and heated to 95° C. This mixture was then added to 11.7 g of 2-vinylnaphthalene (Aldrich Chemical Co., Milwaukee, Wis., purified by sublimation and chromatography on basic alumina in a dichloromethane solution), 300 mg of sodium bicarbonate and 90 mg of potassium persulfate. As soon as the 2-vinylnaphthalene had metered, 4 mL of 10% sodium dodecyl sulfate was fed into the mixture at a rate of 0.3 mL/min. One hour after the beginning of the SDS feed, the polymerization was complete. The optical density of the product measured at 340 nm was 0.155 after diluting 1:5000 in water. The average particle diameter was determined to be 74 nm by electron microscopy. The conversion of monomer to polymer was found to be 99.6% by gas chromatographic determination of the residual monomer.

An outer shell of polyglycidylmethacrylate was formed on the polyvinylnaphthalene/polystyrene particles. Polymerization of glycidyl methacrylate was carried out in the same apparatus as above. One hundred four mL of the polyvinylnaphthalene/polystyrene particles was heated in a boiling water bath. One hundred milligrams of potassium persulfate and 2.06 mL of glycidylmethacrylate (Aldrich Chemical Co.) were added. After 20 minutes, the mixture was cooled. The conversion of monomeric glycidyl methacrylate to polymer was found to be 99.0% by determination of the unreacted monomer concentration. The optical density of the product measured at 340 nm was 0.154 after diluting 1:5000 in water.

D. Attachment of NHB to Polymer Particles

An analog of o-nitrophenol, 3-nitro-4-hydroxy benzoic acid (NHB, 144 mg) and 1-ethyl-3-(3-dimethylaminopropyl) carbodiimide (156 mg) were dissovled in 5 mL of dimethylsulfoxide and allowed to sit at room temperature for 2 hours. In a second 5 mL volume of dimethylsulfoxide was dissolved 420 mg of 2,2'-oxybis (ethylamine) dihydrochloride. The two solutions were then combined and allowed to incubate at room temperature for approximately 72 hours.

The NHB conjugate solution (0.333 mL), prepared as described above, and 0.06 mL of a 10% w/v GAFAC® RE-610:water solution (GAFAC® RE-610 is an anionic surfactant from GAF Corp., N.Y.) were diluted in 4.4 mL of 5 mM sodium phosphate buffer (pH 8.8). The pH of the solution was adjusted to pH 10.0–10.1 and 1.2 mL of core/shell polymer particles (part C above) were added to the reaction. The mixture was heated to 70° C. for 3 hours and allowed to cool to room temperature. The particle reagent was diluted with 15 mM sodium phosphate buffer (pH 7.0) containing 0.1% GAFAC®. The particles were centrifuged for 90 minutes at 20,000 rpm to form a pellet, and the supernatant was discarded. The particles were resuspended in the phosphate/GAFAC® solution and recentrifuged. The centrifuge and resuspension process was repeated a total of four times to remove unreacted NHB conjugate. After the final wash, the particle reagent was brought to a total volume of 10 mL in the 15 mM sodium phosphate buffer (pH 7.0) containing 0.1% GAFAC®.

E. β-galactosidase Activity (Prior Art)

All assays were performed at 37° C. on the aca® discrete clinical analyzer (Du Pont Co., Wilmington, Del.). A stock solution of the enzyme β-galactosidase (Sigma Chemical Co., St. Louis, Mo.) was prepared at a concentration of $4.5 \times 10^3$ units/mL based on the activity as determined by the manufacturer. Serial dilutions of the stock β-galactosidase solution were prepared over the range $4.5 \times 10^3$–$4.5 \times 10^{-3}$ units/mL. A 0.05 mL sample of each β-galactosidase dilution was injected automatically into an aca® analytical test pack followed by 4.95 mL of a 0.15M phosphate buffer (pH 7.8) containing 3% polyethylene glycol 8000, 0.1% GAFAC®, and 2 mM magnesium chloride. The contents of the pack were then heated to 37° C., and the enzymatic reaction was initiated by the addition of o-nitrophenyl-β-D-galactopyranoside (ONPG) to a final concentration of 0.1 mM. Enzymatic activity was determined by measuring the difference in the absorbance at 405 nm (rate of change) 29 seconds and 46 seconds after the ONPG addition.

F. β-galactosidase Activity Using the Agglutination Inhibition Mode of the Present Invention The β-galactosidase serial dilutions prepared in part E above also were used for these experiments. A 0.05 mL sample of each β-galactosidase dilution was automatically injected into an aca® analytical test pack followed by 4.95 mL of a 0.15M phosphate buffer (pH 7.8) containing 3% polyethylene glycol 8000, 0.1% GAFAC®, and 2 mM magnesium chloride. The contents of the pack were heated to 37° C., and the reagents in the first four pack dimples were released. The reaction mixture at this point consisted of 0.1 mM ONPG and 0.016% solids of the NHB particle reagent synthesized in part D above. The turbidimetric inhibition reaction was initiated 3.5 minutes later by the addition of 0.008 mL of rabbit anti-NHB antiserum prepared in part B above. The increase in turbidity due to particle aggregation was measured as the difference in the absorbance at 405 nm (rate of change) 29 seconds and 46 seconds after antibody addition. Table 3 shows the data for β-galactosidase activity comparing the prior art method and the method of this invention.

The data show that the prior art method had a sensitivity of between 0.25 and 2.5 units/mL, while the method provided by the present invention had a sensitivity of about $2.5 \times 10^{-4}$ units/mL, which corresponds to almost a thousand-fold increase.

TABLE 3

β-Galactosidase Activity Measurements

| β-Galactosidase Activity in Assay Units/mL | Prior Art (mA/min at 405 nm) | Present Invention (mA/min at 405 nm) |
|---|---|---|
| 25 | 647 | nd |
| 2.5 | 53 | nd |
| 0.25 | 2 | 12 |
| 0.025 | 0 | 56 |
| 0.0025 | 0 | 151 |
| 0.00025 | 0 | 184 |
| 0 | 0 | 186 | nd = not determined

EXAMPLE 2

Measurement of Digoxin

The following example illustrates the ability of the method provided by the present invention to measure as little as 0.5 ng/mL of digoxin in a test sample. In the example, which illustates the second aspect of the invention, the analyte was digoxin. The first binding partner was an anti-digoxin F(ab')$_2$ antibody fragment which was covalently coupled to the enzyme β-galactosidase to form the conjugate. The separation of bound conjugate from free conjugate was effected using an affinity column containing beads of cross-linked dextran having ouabain coated thereon. The highly refractive particles contained a polystyrene core with an intermediate shell of polyvinylnaphthalene and an outer shell of polyglycidyl methacrylate. The ligand was 4-amino-2-nitrophenol. The second binding partner was a monoclonal antibody prepared against an immunogen comprising 3-nitro-4-hydroxybenzoic acid coupled to keyhole limpet hemocyanin; the antibody was highly cross-reactive with o-nitrophenol. The substrate was ortho-nitrophenyl-β-D-galactopyranoside. The method was performed in the agglutination inhibition mode. The rate of agglutination was determined by measuring optical density at 405 nm at two predetermined times.

A. Synthesis of Antibody-Enzyme Conjugate

Digoxin-specific antibodies were immunopurified directly from whole rabbit serum using a ouabain-human serum albumin (HSA) immunoadsorbant.

Ouabain was attached to an agarose matrix through a protein (HSA) spacer arm. The first step involved the synthesis of a ouabain-albumin conjugate. Ouabain (0.56 mmol dissolved in 20 mL of water) was oxidized with sodium metaperiodate (1.02 mmol) for 1 hour at room temperature in the dark. Quantitative oxidation was verified by thin layer chromatography on silica gel G plates developed in ethylacetate:methanol:$H_2O$ (75:25:1). The excess periodate was removed by passing the aqueous mixture over a 3 mL column of DOWEX AG-1X8 ion exchange resin. Quantitative recovery of ouabain was verified by following radiolabeled (tritiated) ouabain. The solution of oxidized ouabain was buffered to pH 9.5 with the addition of 0.4 mL of 5% $Na_2CO_3$ and combined with 20 mL of HSA solution (28 mg/mL). After 45 minutes, the conjugate was reduced by the addition of 0.3 gm of sodium borohydride freshly dissolved in 20 mL of water. Three hours later, 8 mL of 1 M formic acid was added to lower the pH to 6.5. After 1 hour at pH 6.5, the pH was raised to pH 7.5 with 1 M $NH_4OH$. The entire reaction mixture was dialyzed exhaustively against distilled water, and then finally against 0.015 M sodium phosphate buffer, pH 7.8, 0.15 M NaCl. The conjugate was concentrated on an Amicon PM-30 membrane to 4.2 mg/mL. Protein concentration was determined by the method of Lowry, which is well known in the art.

The ouabain-HSA conjugate was immobilized on Affi-Gel® 10 (Bio-Rad Laboratories, Richmond, Calif.) using the procedure described in the Bio-Rad manual. Affi-Gel® 10 (25 mL) was washed with 75 mL of ice-cold water. The gel was added to the dialyzed ouabain-HSA conjugate and allowed to mix on a rocker overnight at 4° C. The excess active ester groups were quenched by adding 0.1 mL of 1 M ethanolamine, pH 8.0, for 1 hour at room temperature. Finally, the gel was washed extensively with distilled water, and then in turn: 500p mL of 0.5 M NaCl; 400 mL 0.1 M glycine, pH 2.5; 300 mL 2.5 M $NH_4SCN$; 1000 mL phosphate buffered saline. The ouabain affinity resin was packed into a column (0.7 × 15 cm) to a bed volume of 6 mL and equilibrated with phosphate-buffered saline. Anti-serum (10 mL of Cappel anti-digoxin serum at 4.5 mg/mL monospecific antibody) was applied at a flow rate of 1 mL per minute. The column was washed with phosphate-buffered saline until the absorbance at 280 nm reached baseline ( 0.01). Antibody was then eluted from the column with 60 mL of M $NH_4SCN$ (pH 7.5) and immediately dialyzed against 4×2 L changes of phosphate-buffered saline at 4° C.

Affinity-purified anti-digoxin antibodies (27 mL) were concentrated to 2.7 mL on an Amicon stirred-cell apparatus (PM-30 membrane). The final protein concentration was 10 mg/mL. The sample was dialyzed against 1000 mL of 0.1 M sodium acetate, pH 4.5, for 4 hours at 4° C. After dialysis, 0.02 mL of a 10 mg/mL solution of pepsin, dissolved in the same sodium acetate buffer, was added and the temperature raised to 37° C. for 20 hours. After this digestion period, the sample was clarified by a brief centrifugation and then chromatographed on a Sephadex G-150 column (1.5×90 cm) equilibrated on 0.015 M sodium phosphate (pH 7.4), 0.15 M NaCl (phosphate-buffered saline). The column fractions containing the F(ab')$_2$-fragments, identified by gel electrophoresis, were pooled (19.2 mL) and then concentrated to 2.7 mL by pressure filtration (PM-30 Amicon membrane).

One milliliter of affinity-purified anti-digoxin F(ab')$_2$-fragments (2.85 mg/mL protein in 0.015 M sodium phosphate, 0.15M NaCl, 1 mM EDTA, pH 7.0) was mixed at 23°–25° C. with 0.0091 mL of a 60 mM solution of succinimidyl 4-(N-maleimido-methyl) cyclohexane-1-carboxylate (SMCC) dissolved in dimethylformamide. After 60 minutes, the reaction was stopped by desalting the solution on a Sephadex G-25 column (1.5×30 cm) equilibrated in the same sodium phosphate-NaClEDTA solution. The protein which eluted in the void volumn was collected and concentrated to 1 mL using an Amicon stirred cell concentrator (PM-30 membrane). Twenty-four mg of β-galactosidase dissolved in 1 mL of 0.05 M Tris HCl, 0.15 M NaCl, 1 mM $MgCl_2$, pH 7.5 was added to the F(ab')$_2$-SMCC adduct and allowed to react for 20 hours at 4° C. The reaction was quenched by the addition of 0.01 mL of a 0.1 M solution of 2-mercaptoethanol for 1 hour at 4° C. The F(ab')$_2$-β-galactosidase conjugate was separated from the unreacted β-galactosidase by chromatography on a Sepharose 4B column (1.5×90 cm) equilibrated in 0.05 M Tris-HCl, 0.15 M NaCl, 1 mM $MgCl_2$, pH 7.5 at 4° C.

B. Synthesis of Ouabain Resin

Ouabain was coupled to Sephadex G-10 at optimized ratios via bovine serum albumin (BSA).

Ouabain-BSA was prepared by dissolving 5 g of ouabain octahydrate in 500 mL of hot distilled water (70° C.). After the solution was allowed to cool to 25° C., 7.3 g of sodium metaperiodate was added followed by continuous mixing for 2 hours at 25° C. in the dark. The oxidation was then stopped by passing the mixture through a 250 mL bed of Dowex (1X8) anion exchange resin. The eluate was collected and combined with a solution of bovine serum albumin (10 g/500 mL) dissolved in 1 M sodium phosphate buffer, pH 7.0 After 1 hour at 25° C., 0.64 g of sodium cyanoborohydride was added with stirring and the mixture was allowed to incubate for 72 hours at 25° C. The uncoupled ouabain was removed from the mixture by dialyzing the ouabain-BSA conjugate solution against running distilled water for 24 hours and then against 20 volumns of 0.015 M sodium phosphate buffer, pH 7.0 at 4° C. The final ionic strength of the conjugate solution was adjusted to 0.25 M by adding 14.6 g of NaCl prior to coupling to the Sephadex resin.

Sephadex G-10 (420 g) (Pharmacia Fine Chemicals, Piscataway, N.J.) was allowed to swell in 2000 mL of distilled water for 1 hour. Resin fines were removed by decantation and resuspension with 3×2000 mL of water. The resin was then oxidized by resuspension in 1000 mL of water containing 20 g of dissolved sodium metaperiodate. After 10 minutes, the resin was washed with 5×2000 mL of water followed by 4000 mL of 0.25 M sodium phosphate buffer, pH 7.0. The decanted resin was resuspended in 1000 mL of the ouabain-BSA solution (from above), allowed to mix for one hour at 25° C., and then mixed with 0.66 g of sodium cyanoborohydride. After 72 hours, the resin was washed thoroughly with 4000 mL of 0.1% sodium dodecyl sulfate in water, 12 L of distilled water, and then 4000 mL of 0.15 M sodium phosphate buffer, pH 7.1. The final resin was slurry packed into small columns (0.5×7 cm) for use in automated analysis on the Du Pont aca discrete clinical analyzer.

C. Monoclonal Anti-NHB Antibodies

Synthesis of a 3-nitro-4-hydroxybenzoic acid/KLH conjugate used for the development of antibodies cross-reactive with o-nitrophenol is described in Example 1, Part A.

1. Mouse Immunization

Two BALB/C mice were injected intraperitoneally with 0.1 mg each of NHB-KLH emulsified in 0.25 mL of complete Freund's adjuvant (total volume of 0.5 mL per mouse). Five booster injections were given at 21 day intervals (0.1 mg of NHB-KLH in incomplete Freund's adjuvant). A sixth boost was given 49 days after the fifth booster. The final (7th) boost was given 21 days after the sixth boost. Fusion was done four days after final boost.

2. Fusion

Spleens were removed aseptically, and a single cell suspension prepared by passing the spleens through a wire mesh. Spleen cells were fused with $3.5 \times 10^7$ P3Ag8.653 murine myeloma cells (ratio of 4.5:1 spleen cells to myeloma cells). The fusion was done by the addition of 1.8 mL of a polyethylene glycol (PEG) solution (42% v/v PEG 3350, 45.2% media and 7.5% dimethylsulfoxide) to the pellet of myeloma and spleen cells that had been washed in serum free media. The mixture was allowed to stand for one minute. One mL of serum free media was then added slowly over one minute. Forty mL of serum free media was then added over five minutes. Feeder cells (peritoneal exudate macrophages) in 40 mL of Iscove's medium containing HAT (hypoxanthine, aminopterin, and thymidine) and fetal calf serum was added. The total 80 mL was plated into twenty 96 well microtiter plates. Clones were detected after one week in culture (7% $CO_2$ incubator).

3. Screening

Supernatants were harvested four weeks after the fusion. They were screened for antibody activity using a particle enhanced turbidimetric immunoassay (U.S. Pat. No. 4,401,765). Supernatants (0.025mL) were added to microtiter wells containing 0.075 mL of buffer (150 mM phosphate, 3% PEG 8000, 0.1% GAFAC®, 2 mM $MgCl_2$) containing NHB particle reagent (0.05 mL particle reagent from Example 1, Part D, to 10 mL buffer) pH 7.8. The contents of the plate were incubated at 37° C. for five minutes and then examined for agglutination of the particles. A total of nine positive cell lines were detected from 70 clones. These supernatants were then screened for their ability to bind free NHB-BSA by the addition of NHB-BSA to the particle reagent-buffer in the microtiter well before addition of the culture supernatants. All nine clones showed inhibition of agglutination (lack of turbidity) when this was done.

4. Cloning

The cell lines were cloned at semi-limiting dilution, approximately 1 cell per well. An aliquot of cells was also frozen in liquid nitrogen as a safeguard against loss. Feeder cells (peritoneal macrophages) were used to promote growth. When clones were large enough, culture supernatants were retested for antibody as described in Part C (3) above.

The cells of interest were then selected for cloning at limiting dilution, using strict Poisson statistics. When sufficient numbers of cells were present in the wells, the supernatants were again tested for antibody. The reclones were then frozen for storage.

5. Chain Composition

The heavy chain composition of the antibodies produced by the following cell lines was determined by double diffusion in agar gel using specific reagents.

| Cell Line | Heavy Chain Isotype |
| --- | --- |
| 2/1 | $\gamma_3$ |
| 2/2 | $\gamma_1$ |
| 2/3 | $\gamma_1$ |
| 2/4 | $\gamma_1$ |
| 2/5 | $\gamma_1$ |
| 2/6 | $\gamma_b$ |
| 2/7 | $\gamma_1$ |
| 2/8 | $\gamma_1$ |

D. Attachment of an NHB Analog to Polymer Particles

A 0.5 M solution of 4-amino-2-nitrophenol (ANP) was made by dissolving 385 mg in 5 mL of dimethyl sulfoxide. The 0.5 M ANP solution (0.2 mL) was added to 9.75 mL of 5 mM sodium phosphate (pH 8.0) with 0.12 mL of 10% GAFAC®. The pH of the mixture was adjusted to 10.0–10.1. Then 1.93 mL of core/shell polymer particles (Example 1, Part C) were added to the ANP mixture was heated to 70° C. for 3 hours. The resulting particle reagent was washed by diluting in 15 mM sodium phosphate, 0.1% GAFAC® (pH 7.0) and centrifuging for 90 minutes at 20,000 rpm in a refrigerated centrifuge. The washing procedure was done a total of five times. After the final wash, the particle reagent pellet was brought up to a total volume of 10 mL in the 15 mM sodium phosphate buffer, 0.1% GAFAC® (pH 7.0). The particle reagent was dialyzed against two liters of the phosphate/GAFAC® wash buffer overnight.

E. Digoxin Assay Using Affinity Column Mediated Immunoassay

All assays were performed at 37° C. on the aca® discrete clinical analyzer. Equal volumes of the human serum sample containing digoxin and the antibody-enzyme conjugate prepared in part A above were mixed and incubated at 25° C. for 15 minutes. After incubation, a 0.4 mL aliquot of the sample mixture was automatically injected into an aca® analytical test pack and eluted through the column (part B above) in the pack header. Sample was followed by 2 mL of 0.15 M phosphate buffer, pH 7.8. The column elution rate was 0.034 mL/sec. The pack was then filled at needle position 2 (which bypasses the column) with an additional 2.60 mL of water. The contents of the pack were then heated to 37° C. and the reagents in the first four pack dimples were released. The reaction mixture at this point consisted of 100 mM HEPES buffer, 50 mM phosphate buffer (pH 7.6) and 2 mM magnesium chloride. The enzymatic reaction was initiated 3.5 minutes later by the addition of ONPG to a final concentration of 2 mM in the reaction mixture. Enzymatic activity was determined by measuring the difference in the absorbance at 405 nm (rate of change) 29 seconds and 46 seconds after ONPG addition.

F. Amplification of the Digoxin Assay Using Particle Agglutination Inhibition All assays were performed at 37° C. on the aca® discrete clinical analyzer. Equal volumes of the serum sample and the antibody-enzyme conjugate prepared in part A above were mixed and incubated at 25° C. for 15 minutes. After incubation, a 0.04 mL aliquot of the sample mixture was automatically injected into an aca® analytical test pack and eluted through the column (part B above) in the pack header. Sample was followed by 2 mL of 0.15 M phosphate buffer, pH 7.8. The column elution rate was 0.034 mL/sec. The pack was then filled at needle position 2 (which bypasses the column) with an additional 2.96 mL of 0.15 M phosphate buffer, pH 7.8. The contents of the pack were then heated to 37° C. and the reagents in the first four pack dimples were released. The reaction mixture at this point consisted of 4.96 mL of 0.15 M phosphate buffer (pH 7.8), 0.1% GAFAC® 1.46% (w/v) PEG 8000 and 0.02% (w/v) solids of the polymer particle (part D above). The turbidimetric inhibition reaction was initiated 3.5 minutes later by the addition of monoclonal anti-NHB ascites fluid (0.009 mL, Clone 2/4). The increase in turbidity due to particle aggregation was measured as the difference in the absorbance at 405 nm (rate of change) 29 seconds and 46 seconds after antibody addition. Table 4 shows data comparing unamplified immunoassay results and amplified results using the method of the present invention. The comparison shows that the present invention can decrease sample size ten-fold while at the same time increasing signal production by approximately 5-fold.

TABLE 4

| Digoxin Concentration (ng/mL) | Digoxin Standard Curves | |
| --- | --- | --- |
| | Unamplified Assay* Rate (mA/min at 405 nm) | Amplified Assay** Rate (mA/min at 405 nm) |
| 0 | 36 | 474 |
| 0.5 | 54 | 394 |
| 1.5 | 98 | 212 |
| 2.5 | 134 | 129 |
| 3.5 | 148 | 127 |

*400 μL sample size
**40 μL sample size

EXAMPLE 3

Measurement of Human Chorionic Gonadotropin (hCG)

The following example illustrates the ability of the method provided by the present invention to measure clinically significant levels of the analyte human chorionic gonadotropin (hCG) in a test sample.

The first binding partner was an anti-β-hCG antibody. The separation of bound conjugate from free conjugate was effected using an affinity column containing a solid support having hCG coated thereon. The highly refractive particles contained a polystyrene core with an intermediate shell of polyvinylnaphthalene and an outer shell of polyglycidyl methacrylate. The ligand was 4-amino-2-nitrophenol. The second binding partner was a monoclonal antibody prepared against an immunogen comprising 3-nitro-4-hydroxybenzoic acid coupled to keyhole limpet hemocyanin; the antibody was highly cross-reactive with o-nitrophenol and 4-amino-2-nitrophenol. The substrate was ortho-nitrophenyl-β-D-galactopyranoside. The method was performed in the agglutination inhibition mode. The rate of agglutination was determined by measuring optical density at 405 nm at two predetermined times.

A. Synthesis of Antibody-Enzyme Conjugate

Six milligrams of β-D-galactosidase (EIA grade, Boehringer-Mannheim Corp., Indianapolis, Ind.) was dissolved in 3 mL of 0.05 M Tris HCl, pH 7.0, 0.14 M NaCl, 1 mM MgCl$_2$, 5 mM EDTA and then mixed with 14.7 μg of o-phenylene-dimaleimide dissolved in 1.1 μL of N,N'-dimethylformamide. After 16 hours at 4° C., the mixture was chromatographed on a Sephadex G-25 column (1.5×40 cm) using the same Tris-NaCl-MgCl$_2$-EDTA buffer described above. The polymerized β-D-galactosidase was pooled from the void volume fractions.

One millimeter (0.89 mg) of monoclonal IgG antibody to β-human chorionic gonadotropin (β-hCG, Hybritech Corporation, San Diego, Calif.) was dialyzed against 1 L of 0.015 M sodium phosphate, pH 7.0, 0.15 M NaCl, 1 mM EDTA at 4° C. for 16 hours. After dialysis, the antibody was reacted with 59 μg of succinimidyl-4-(N-maleimido-methyl) cyclohexane-1-carboxylate dissolved in 5.9 μL of N,Nβ-dimethylformamide for 1 hour at 20°–23° C. The reaction was terminated by passing the mixture over a Sephadex G-25 column (1.5×40 cm) equilibrated in 0.015 M sodium phosphate, pH 7.0, 0.15 M NaCl, 1 mM EDTA. The maleimido-IgG adduct eluting in the void volume of the column was pooled and concentrated to 1.13 mL by pressure filtration.

The conjugation was performed by combining 1.13 mL (0.61 mg/mL) of the maleimido-IgG with 5.73 mL of the polymerized β-D-galactosidase (0.87 mg/mL) and mixing for 20 hours at 4° C. The mixture was concentrated to 2.0 mL by pressure filtration and then chromatographed on a Sepharose 4B column (1.5×90 cm) equilibrated in 0.05 M Tris HCl, pH 7.5, 0.15 M NaCl, 0.0001 M MgCl$_2$, at 4° C. The IgG-β-galactosidase conjugate eluted in the void volume of the column as confirmed by a microtiter plate ELISA assay for β-hCG. This material was pooled and used in part C below.

B. Synthesis of hCG Resin

Human chorionic gonadotropin (hCG) from Organon, Inc., West Orange, N.J., was coupled to 1,1'-carbonyldiimidazole activated Fractogel TSK HW-65F (Pierce Chemical Co., Rockford, Ill.). hCG (19.2 mg) was dissolved in 40 mL 0.1 M sodium carbonate buffer pH 8.5 and dialyzed against this buffer. Forty mL of the resin solids was washed with one liter of the cold carbonate buffer. The dialyzed hCG solution was added to the gel and allowed to mix on a rotator overnight at 4° C. The gel was then washed with the carbonate buffer to remove unbound hCG. Any remaining active groups on the resin were blocked by adding 80 mL of 0.1 M glycine in 0.05 M Tris buffer pH 7.5 and incubating overnight at 4° C. Finally, the resin was washed exhaustively with 0.05 M Tris (pH 7.5) containing 0.01% sodium azide.

C. hCG Assays Using Affinity Column Mediated Immunoassay

Antibody-enzyme conjugate from part A above (0.015 mL) was added to 1.2 mL of separate samples containing various concentrations of hCG. Calibrators were prepared by dissolving hCG in 0.05 M Tris buffer (pH 7.2) containing 0.5% human serum albumin. After a one hour room temperature incubation period, 0.5 mL of the mixture was processed through a 2 mL hCG column (part B above) with 1.2 mL of 0.15 M phosphate buffer pH 7.1 at a flow rate of 0.01 mL per second. The 1.7 mL fraction was collected containing any antibody enzyme conjugate that did not bind to the column.

All measurements of antibody-enzyme conjugate activity were performed on the Du Pont aca ® discrete clinical analyzer at 37° C. The 1.7 mL column fraction was added to 3.3 mL of 0.1 M sodium phosphate pH 7.8 containing 1 mM magnesium chloride. The reaction was initiated after a 1.5 minute incubation by the addition of 2.8 mg of ONPG and 0.11 mL of 3.4 M $\beta$-mercaptoethanol. The absorbance due to the production of ortho-nitrophenol by the antibody-enzyme conjugate was measured as the difference in absorbance at 405 nm minus 600 nm (endpoint measurement) 3.5 minutes after reaction initiation.

D. Amplification of the hCG Assays Using Particle Agglutination Inhibition

Incubation of the antibody-enzyme conjugate and separation on the hCG resin were performed as described in part C. All measurements of antibody-enzyme conjugate activity were performed on the Du Pont aca ® discrete clinical analyzer at 37° C. The 1.7 mL column fraction was collected and a 0.02 mL aliquot was added to 4.98 mLs of 0.15 M phosphate buffer pH 7.8 containing 1.46% PEG 8000, 0.1% GAFAC ®, 0.06% ONPG and 2mM $MgCl_2$. Mouse monoclonal anti-NHB ascites fluid (0.02 mL, Clone 2/8) was added and the reaction was initiated after a 3.5 minute incubation period by the addition of 0.05 mL of the ANP particle reagent containing 2.4% solids (Example 2, part D). The increase in turbidity due to particle aggregation was measured as the difference in absorbance at 406 nm (rate of change) 29 seconds to 46 seconds after reaction initiation.

TABLE 5

| hCG Concentration (mIU/mL) | hCG Standard Curves Unamplified Assay Endpoint* Absorbance at (405 nm–600 nm) | Amplified assay Rate** mA/min at 405 nm |
| --- | --- | --- |
| 0 | 0.2379 | 244 |
| 5 | 0.2679 | 241 |
| 10 | 0.2997 | 214 |
| 25 | 0.3794 | 161 |
| 50 | 0.5998 | 82 |
| 100 | 1.0500 | 13 |

*Assay utilized 1.7 mL column eluate.
**Assay utilized 0.02 mL column eluate.

The table compares data from an optimized, unamplified end-point determination and from an optimized particle agglutination assay (i.e., rate determination). The comparative data show that the method of this invention provides good sensitivity, even with 85-fold less antibody-enzyme conjugate participating in the agglutination reaction than that participating in the unamplified reaction.

EXAMPLE 4

Measurement of Human Chorionic Gonadotropin (hCG)

Synthesis of the antibody-enzyme conjugate included in the following example is described in Example 3, part A. The ANP particle reagent and the anti-NHB antibodies are described in Example 2, parts C and D, respectively.

A. hCG Sandwich Assays (Prior Art)

Plastic beads coated with a monoclonal antibody directed toward an antigenic site on the hCG molecule were obtained from the Tandem TM -E HCG kit available commercially from Hybritech Incorporated, San Diego, CA. hCG standards were prepared by diluting the 200 mIU/mL Tandem TM -E calibrator with the zero diluent supplied with the Tandem TM -E kit. The antibody-enzyme conjugate (0.005 mL) and 0.1 mL of either serum hCG sample or hCG standard were added to a plastic tube containing one Tandem TM -E antibody bead prewashed with 0.15 M phosphate buffer (pH 7.8) containing 0.15 GAFAC ®. Mixing occurred by rotation at 170 rpm for thirty minutes at room temperature. The bead was then washed in the tube with six successive 2.0 mL volumes of the 0.15 M phosphate, 0.1% GAFAC ® buffer followed by three 2.0 mL washes with 0.15 M phosphate pH 7.8 containing 1 mM $MgCl_2$. After the final wash was decanted, 1.0 mL of 0.06% ONPG dissolved in the 0.15 M phosphate, 1.2 mM $MgCl_2$ buffer was added to the bead. After a thirty minute room temperature incubation, the reaction was quenched by removal of the liquid from the bead. Absorbance due to the production of ONP by the antibody-enzyme conjugate bound to the bead was measured at 406 nm on the Hewlett-Packard 8450 A spectrophotometer.

B. Amplification of the hCG Sandwich Assay Using Particle Agglutination Inhibition The antibody-enzyme conjugate (0.002 mL) and serum hCG sample (0.1 mL) were added to a plastic test tube containing one Tandem TM -E antibody bead prewashed with 0.15 M phosphate buffer (pH 7.8) containing 0.1% GAFAC ®. Mixing was carried out by rotation at 170 rpm for 90 minutes at room temperature. The bead was washed in the tube with six successive 2.0 mL volumes of the 0.15 M phosphate, 0.1% GAFAC ® buffer, followed by three 2.0 mL washes with 0.09 M phosphate (pH 7.8) containing 9.1 mM $MgCl_2$. After the final wash was decanted, 0.2 mL of 0.06% ONPG dissolved in the 0.09 M phosphate, 1.2 mM $MgCl_2$ buffer was added to the bead. Substrate turnover to ONP by bound conjugate occurred during a 10 minute incubation at room temperature. The ONP sample was obtained by removing the liquid from the bead after the incubation period. (The ONP concentration was directly proportional to the concentration of hCG in the sample.) hCG standards were prepared as described in part A.

All measurements of ONP concentration in the bead supernatants were performed at 37° C. on a Cobas Bio Automated Centrifugal Analyzer (Roche Diagnostic Systems, Nutley, N.J.). The ONP sample (0.08 mL) was added to 0.12 mL of 0.15 M phosphate buffer (pH 7.8) containing 1.5% PEG 8000, 0.1% GAFAC ®, 2 mM $MgCl_2$ and 0.05% solids of ANP particle reagent (Example 2, part D). The reaction was initiated after a 60 second incubation period by the addition of 0.001 mL anti-NHB mouse monoclonal ascites fluid (Clone 2/7). The increase in turbidity due to particle aggregation was measured as the difference in absorbance at 405 nm (rate of change) 10s to 20s after initiation. Table 6 shows the data for serum hCG standard curves comparing the sandwich and particle amplified sandwich technologies.

TABLE 6 hCG Standard Curves

| hCG Concentration (mIU/mL) | Unamplified Assay Endpoint (milliabsorbance at 406 nm) | Amplified Assay Rate (mA/min at 405 nm) |
|---|---|---|
| 0 | 40 | 456 |
| 0.2 | nd | 442 |
| 0.5 | nd | 342 |
| 1.0 | nd | 305 |
| 2.0 | nd | 218 |
| 5.0 | 62 | 36 |
| 10.0 | 68 | 16 |
| 25.0 | 101 | nd |
| 50.0 | 170 | nd |
| 100 | 239 | nd |
| 200 | 408 | nd | nd = not determined

The sandwich assay was first optimized to produce maximum sensitivity over the hCG concentration range examined, and then the particle amplification system was optimized for maximum particle agglutination inhibition over the same hCG range. The data show that the sandwich endpoint assay produces a significant absorbance change corresponding to between 10 and 25 mIU hCG, while the particle amplification system provides a significant absorbance change corresponding to between 0.2 and 0.5 mIU hCG. This represents an approximately fifty-fold sensitivity improvement over the sandwich endpoint assay optimized for chromogenic signal detection.

EXAMPLE 5

The following example illustrates the use of the direct agglutination method provided by the present invention for measuring enzyme activity. In the example, the highly refractive particles have a polystyrene core with an intermediate shell of polyvinylnaphthalene and an outer shell of polyglycidyl methacrylate. The binding agent would be an antibody prepared against the hapten 3-nitro-4-hydroxybenzoic acid. The substrate would be 3-nitro-4-O-(β-D-galactopyranosyl) benzoic acid which can be coupled covalently to the outer shell of the highly refractive particles. The enzyme β-galactosidase would hydrolyze the galactopyranosyl derivative on the particle surface. Direct particle agglutination would then occur in the presence of the binding agent. The extent of agglutination could be observed visually to obtain a qualitative measure of enzyme activity or a change in the physical properties of the solution could be measured instrumentally to supply quantitative results.

A. Synthesis of 3-Nitro-4-O-(β-D-galactopyranosyl) benzoic acid

A substrate for β-galactosidase that is capable of attachment to highly refractive particles is required for the present example. The ligand, 3-nitro-4-O-(β-D-galactopyranosyl) benzoic acid (NGB) would meet this requirement. An example of a procedure that could be adapted for the synthesis of this analog is provided by D. H. Leaback in an appendix to a paper by J. W. Woollen and P. G. Walker. [Clin. Chem. Acta. (1965) 12, 647, 65].

Acetobromogalactose (1g, 2.44 mmole) and 3-nitro-4-hydroxybenzoic acid (0.40g, 2.20 mmole) are dissolved in methanol (10 mL) and 1 N sodium hydroxide (2.2 mL) is added slowly with stirring. The mixture is left for 16 hours at room temperature before the methanol is removed under reduced pressure to leave a syrup. The NGB material would then be deblocked and purified by procedures similar to those described in the above reference.

B. Synthesis of Amine-Modified Polymer Particles

The diamine 2,2-oxybis (ethylamine) dihydrochloride (420mg) and 0.06 mL of a 10% w/v GAFAC®/water solution can be added to 4.7 mL of 5 mM sodium phosphate buffer (pH 8.0). The pH of the solution is adjusted to pH 10.0–10.1 and 1.2 mL of core/shell polymer particles (example 1, part C) are added to the mixture. The solution is heated to 70° C. for 3 hours and allowed to cool to room temperature. The modified particle is diluted with 15 mM sodium phosphate buffer (pH 7.0) containing 0.1% GAFAC®. The particles are centrifuged for 90 minutes at 18,000 rpm to form a pellet, and the supernatant is discarded. The particles are resuspended in the phosphate/GAFAC® solution and recentrifuged. The centrifugation and resuspension process is repeated a total of four times to remove unreacted diamine. After the final wash, the modified particles are brought to a total volume of 1 mL in the phosphate/GAFAC® buffer.

C. Attachment of the NGB Ligand to Amine-Modified Polymer Particles

The NGB substrate described in part A (9.1 mg, 0.026 mmole) is dissolved in 0.17 mL dimethylsulfoxide containing 1-ethyl-3-(3-dimethyl aminopropyl) carbodiimide (5.2 mg, 0.027 mmole) and allowed to sit at room temperature for 2 hours. The NGB solution and 0.06 mL of a 10% w/v GAFAC®/water solution would then be diluted in 2.0 mL of 5 mM sodium phosphate buffer (pH 7.0). The pH of the solution is adjusted to pH 7.0–7.1, and 1.0 mL of the amine-modified core/shell particles (part B above) is added to the reaction. The mixture is cooled to 4° C. and incubated for 16 hours. The particle reagent is diluted with 15 mM sodium phosphate buffer (pH 7.0) containing 0.1% GAFAC®. The particles are centrifuged for 90 minutes at 18,000 rpm to form a pellet, and the supernatant is discarded. The particles are resuspended in the phosphate/GAFAC® solution and recentrifuged. The centrifugation and resuspension process is repeated a total of four times to remove unreacted NGB. After the final wash, the ligand (substrate) particles are brought to a total volume of 10 mL in the phosphate/GAFAC® buffer.

D. β-galactosidase Activity Using the Direct Agglutination Mode of the Present Invention The β-galactosidase serial dilutions as prepared in example 1 (part E) would be appropriate for use in an assay. A convenient volume of each β-galactosidase dilution is added to a mixture consisting of 0.15 M phosphate buffer (pH 7.8), 0.1% GAFAC®, 1.46% w/v PEG 8000 and 0.02% solids w/v of the ligand particles (part C above). Reaction temperature must be equivalent for all assays and is selected as a matter of convenience, preferably between 25° and 37° C. The addition of β-galactosidase to the assay mixture causes hydrolysis of the 3-nitro-4-O-(β-D-galactopyranosyl) benzoic acid on the particle surface to 3-nitro-4-hydroxy benzoic acid. Direct particle agglutination will then occur in the presence of an appropriate concentration of an antibody that binds the hydrolysis product on the particle but does not bind the unhydrolyzed ligand. The anti-NHB antibodies prepared in Examples 1 and 2 above would be appropriate for use in these assays because they have been shown in the previous examples to cause agglutination of 3-nitro-4-hydroxy benzoic acid coupled polymer particles. Direct particle agglutination can occur simultaneously with ligand hydrolysis, providing the anti-NHB antibodies are present prior to or simultaneous with the addition of β-galactosidase. Alternatively, the agglutination reaction can be initiated at any convenient time after β-galactosidase addition by delaying the addition of the anti-NHB antibodies. The extent of particle agglutination can be determined visually or instrumentally, depending on the requirements for qualitative or quantitative results.

We claim:

1. An agglutination based assay for detecting an analyte in a liquid test sample, comprising:
   (1) contacting a sample suspected of containing an analyte with a conjugate comprising an enzyme and a first binding partner capable of binding to the analyte, whereby a fraction of the conjugate binds to the analyte to form a complex and a fraction of the conjugate remains free;
   (2) separating the free conjugate from the complex;
   (3) contacting either the free conjugate or the complex with an agglutination system comprising:
      (i) highly refractive particles having a ligand disposed thereon,
      (ii) a second binding partner capable of binding to at least two ligands, the second binding partner and particle bound ligand being present at concentrations which permit agglutination, and
      (iii) a substrate for the enzyme, wherein said enzyme, said substrate, said ligand and said second binding partner are selected such that a reaction between the enzyme and substrate produces a product which competes with the ligand for the second binding partner;
   (4) measuring a physical property of the agglutination system, which property is a function of agglutination; and
   (5) relating the measurement to the amount of analyte initially present in the sample.

2. The method of claim 1 wherein the enzyme is selected from the group consisting of β-galactosidase, alkaline phosphatase, horseradish peroxidase, glucose oxidase, urease and β-lactamase.

3. The method of claim 1 wherein the first binding partner is an anti-analyte antibody.

4. The method of claim 1 wherein the highly refractive particles are essentially spherical.

5. The method of claim 4 wherein the essentially spherical particles have a diameter in the range of 30 nm to 100,000 nm.

6. The method of claim 5 wherein the diameter is in the range of 30 nm to 100 nm.

7. The method of claim 1 wherein the highly refractive particles comprise a material selected from the group consisting of agarose, polydextran, polyacrylamide, polystyrene, and polyvinylnaphthalene.

8. The method of claim 1 wherein the second binding partner is an antibody having at least two ligand binding sites.

9. The method of claim 1 wherein the enzyme is β-galactosidase, the substrate is ortho-nitrophenyl-β-galactopyranoside, the ligand is 3-nitro-4-hydroxybenzoic acid or ortho-nitrophenol, and the second binding partner is an anti-3-nitro-4-hydroxybenzoic acid antibody.

10. The method of claim 1 wherein the enzyme is alkaline phosphatase, the substrate is para-nitrophenyl phosphate, the ligand is para-nitrophenol, and the second binding partner is an anti-para-nitrophenol antibody.

11. The method of claim 1 wherein the physical property is an optical property.

12. An agglutination-based method for detecting an analyte in a liquid test sample, comprising:
   (1) contacting a sample suspected of containing an analyte with a conjugate comprising an enzyme and a first binding partner capable of binding to the analyte, whereby a fraction of the conjugate binds to the analyte to form a complex and a fraction of the conjugate remains free;
   (2) separating the free conjugate from the complex;
   (3) contacting either the free conjugate or the complex with an agglutination system comprising:
      (i) highly refractive particles having coated thereon a substrate capable of being converted into a ligand upon reaction with the enzyme; and
      (ii) a second binding partner capable of binding to at least two ligands, but incapable of binding to the substrate; and
   (4) measuring a physical property of the agglutination system which is a function of agglutination; and
   (5) relating the measurement to the amount of enzyme initially present in the sample.

13. The method of claim 12 wherein the first binding partner is an anti-analyte antibody.

14. The method of claim 12 wherein the enzyme is selected from the group consisting of β-galactosidase, alkaline phosphatase, horseradish peroxidase, glucose oxidase, urease and β-lactamase.

15. The method of claim 12 wherein the highly refractive particles are essentially spherical.

16. The method of claim 15 wherein the essentially spherical particles have a diameter in the range of 30 nm to 100,000 nm.

17. The method of claim 16 wherein the diameter is in the range of 30 nm to 100 nm.

18. The method of claim 12 wherein the highly refractive particles comprise a material selected from the group consisting of agarose, polydextran, polyacrylamide, polystyrene, and polyvinylnaphthalene.

19. The method of claim 12 wherein the second binding partner is an antibody having at least two ligand binding sites.

20. The method of claim 12 wherein the enzyme is β-galactosidase, the substrate is 3-nitro-4-O-(β-D-galactopyranosyl)benzoic acid and the binding partner is an anti-(3-nitro-4-hydroxy)benzoic acid antibody.

21. The method of claim 12 wherein the physical property is an optical property.

* * * * *